US00PP13531P3

(12) United States Plant Patent
Spink

(10) Patent No.: US PP13,531 P3
(45) Date of Patent: Feb. 4, 2003

(54) CODIAEUM PLANT NAMED 'CROTON ZULU'

(76) Inventor: Gary Spink, 5 Grenaid Court, Wellington Point, Queensland (AU), 4160

( * ) Notice: Subject to any disclaimer, the term of this patent is extended or adjusted under 35 U.S.C. 154(b) by 32 days.

(21) Appl. No.: 09/835,422

(22) Filed: Apr. 16, 2001

(65) Prior Publication Data

US 2002/0002729 P1 Jan. 3, 2002

(30) Foreign Application Priority Data

May 2, 2000 (AU) ..... 2000/126

(51) Int. Cl.[7] ..... A01H 5/00
(52) U.S. Cl. ..... Plt./373
(58) Field of Search ..... Plt./373

*Primary Examiner*—Bruce R. Campell
*Assistant Examiner*—Annette H. Para
(74) *Attorney, Agent, or Firm*—Paul S. Rooy

(57) ABSTRACT

'Croton Zulu', a Codiaeum cutivar. 'Croton Zulu' has a bushy growth habit. It features an uneven variegation beginning yellow (upper surface RHS 5A; lower surface RHS 5D) and maturing to red and orange colors (RHS 59B, RHS 169A, RHS 60A and RHS 17D). When potted in 14 cm pots in shade house conditions, 'Croton Zulu' plants attain a height of 30 cm and are about 30 cm wide, giving the plant a rounded shape.

3 Drawing Sheets

FIELD OF THE INVENTION

Botanical classification: *Codiaeum variegatum.*

Variety denomination: 'Croton Zulu'.

This plant patent application claims foreign priority based on Australian Plant Breeder's Rights application No. 2000/126 filed May 2, 2000.

The present invention comprises a new and distinct cultivar of *Codiaeum variegatum* which is named 'Croton Zulu'. Its market class is that of potted plants or bulbs. *Codiaeum variegatum* 'Croton Zulu' is intended for use in landscaping, and as a decorative potted plant.

DESCRIPTION OF PRIOR ART

'Croton Zulu' was discovered as a sport of Codiaeum 'Mora' in March, 1998 in a greenhouse in Wellington Point, Queensland, Australia. Codiaeum 'Mora' has a bushy growth habit forming a rounded plant, and is distinguished from Codiaeum 'Mora' by much improved leaf variegation and color. 'Croton Zulu' is distinguished from other Codiaeum in general by its bushy growth habit forming a rounded plant, and unique uneven variegation which begins yellow and matures to red and orange colors.

'Croton Zulu' was discovered by Gary R. Spink, 5 Grenaid Court, Wellington Point, Queensland, Australia. 'Croton Zulu' is asexually propagated by cuttings, and has been grown and propagated through numerous generations (at least 6) since March, 1998. During this time the plants as asexually reproduced have remained true to type.

BRIEF DESCRIPTION OF THE DRAWINGS

The invention, together with the other objects, features, aspects and advantages thereof will be more clearly understood from the following in conjunction with the accompanying drawings.

Three sheets of drawings are provided.

Figure 1:
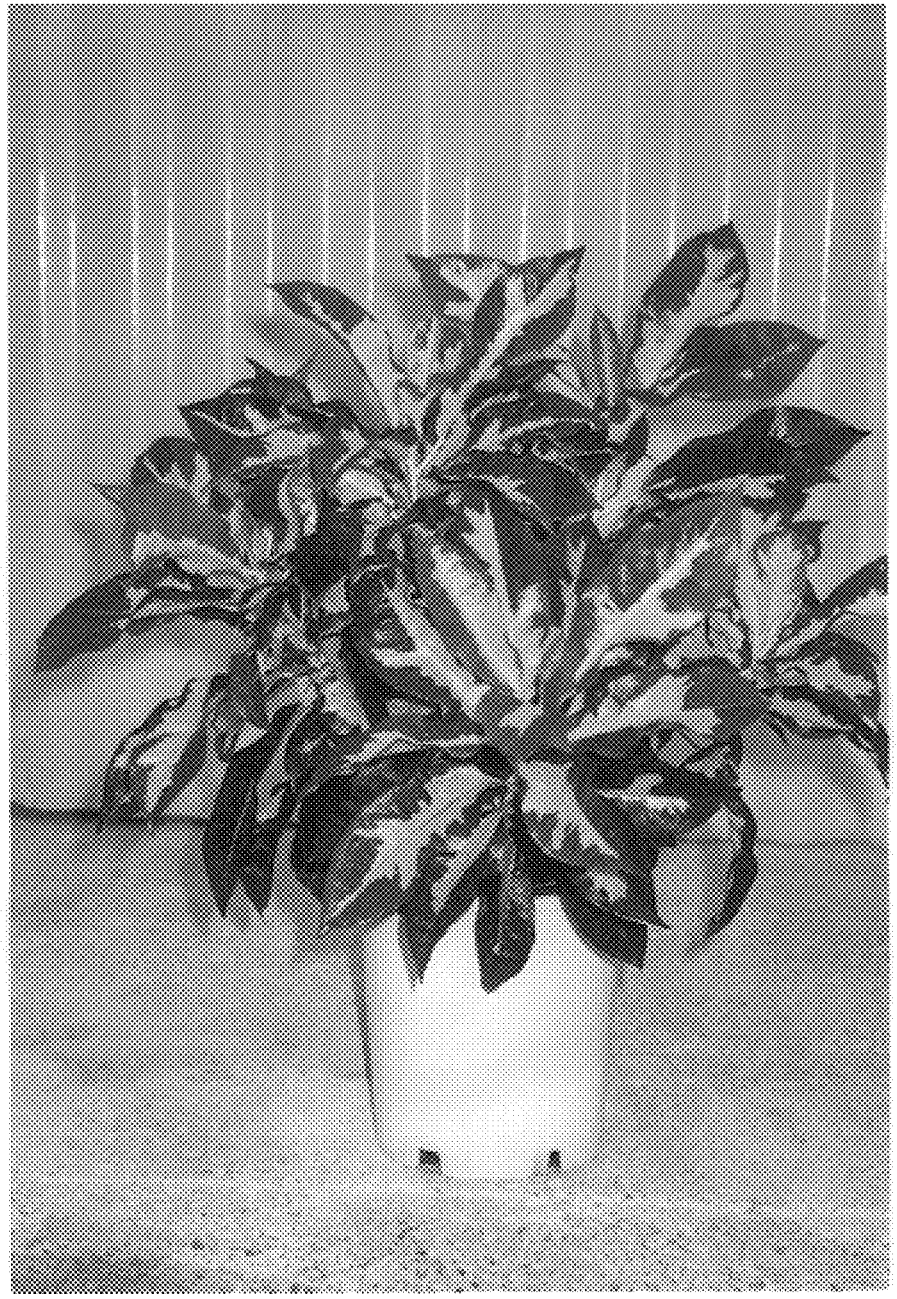

Sheet one contains FIG. 1.

Figure 2:
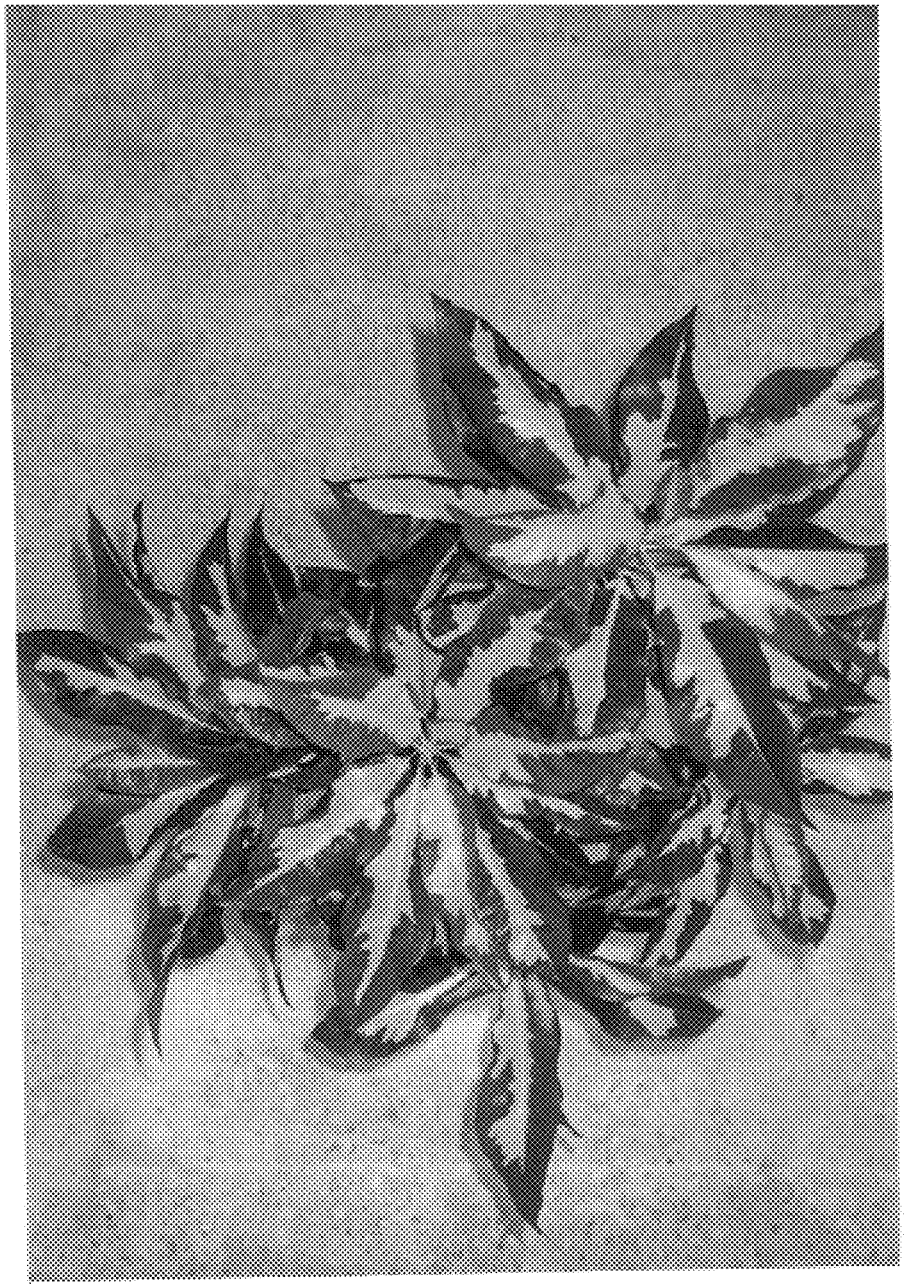

Sheet two contains FIG. 2.

Figure 3:
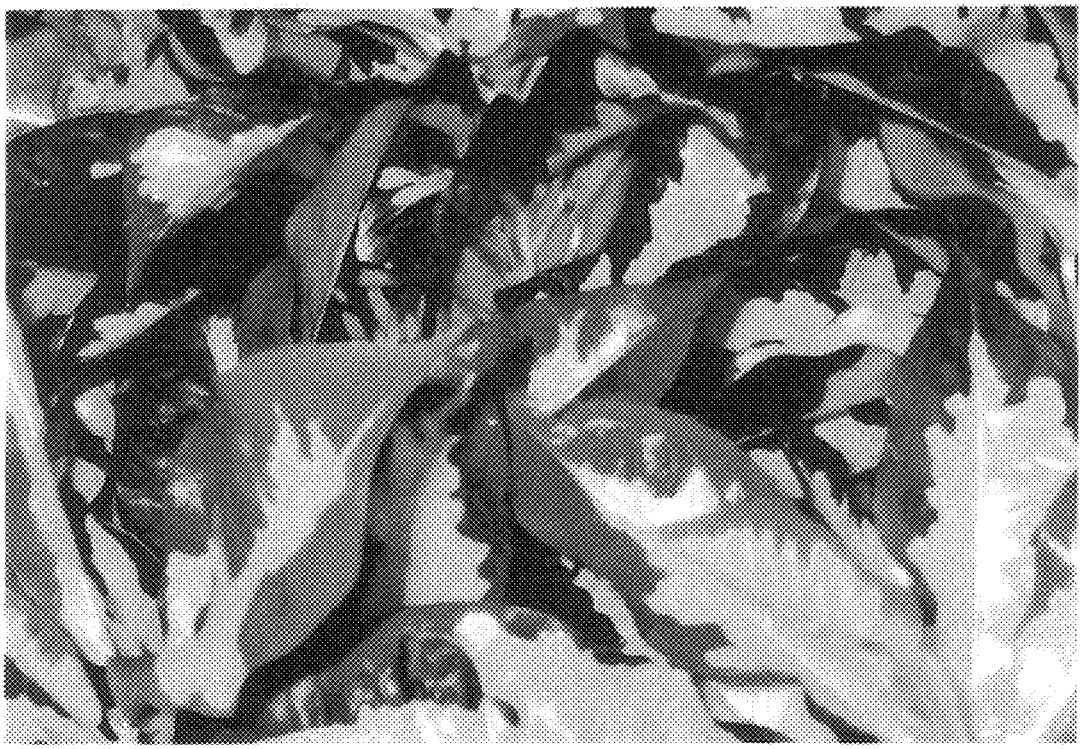

Sheet three contains FIG. 3.

FIG. 1 is a color photograph of a front view of 'Croton Zulu'.

FIG. 2 is a color photograph of a top view of 'Croton Zulu'.

FIG. 3 is a color photograph of a close-up view of 'Croton Zulu' leaves.

BOTANICAL DESCRIPTION OF THE PLANT

'Croton Zulu' is characterized by its bushy growth habit forming a rounded plant and unique uneven variegation beginning yellow and maturing to red and orange colors. It is distinguished from other Codiaeum by the following characteristics:

Plant: A very attractive and unique plant with medium sized leaves with varying degrees of stunning color combination of green, yellow, and red. In 50 mm tubes cutting are ready to pot in about 6–8 weeks. When potted into 14 cm pots in shade house condition, plants attain an approximate height of 30 cm (measured from top of soil level) and are about 30 cm wide as well, giving a rounded shape.

Stem:

*Growth pattern.*—The stem is approximately 0.9 cm in diameter at soil level and branches freely, almost clustered with branch angles from 60 degrees to 90 degrees to the main axis. The side branches grow as strongly as the main stem, giving the plant a rounded appearance.

*Color.*—Emerges mainly yellow RHS 5A with a tinge of green at the tip, changes to tinges of red as for leaf color, and at maturity changes to grayed brown RHS 199D.

Petiole:

*Size.*—Variable, ranging from about 1.2 cm to 2.5 cm.

*Color.*—The emerging petiole is yellow RHS 5A which subsequently fades to about RHS 5D with maturity. The upper surface is slightly darker than lower surface. With maturity at about $3^{rd}$ to $5^{th}$ leaf stage, the lower surface of the petiole develops a red tinge made up of specs colored red purple RHS 59B to RHS 60A.

Leaf:

*Growth pattern.*—The leaf is elliptic with acuminate apex, acute base and entire margin.

*Dimensions.*—The largest leaves are approximately 13 cm×4.5 cm.

*Midrib.*—Prominent and attractive, due to bright colors similar to leaf and stem. Developing leaves have bright yellow midribs with upper surface yellow group RHS 5A and lower surface RHS 5D. Midrib color is same as surrounding blade tissue. With maturity, a red purple tinge RHS 59B to 60A first appears on the lower surface and is darkest on mid ribs, and fades into rest of the leaves.

*Primary veins.*—Same as blade color surrounding them.

*Color and pattern.*—Emerging leaves are green (at least the margins), and the varying degree of yellow appears from midrib outwards. See FIGS. 1 and 2. Yellow portion is very variable but almost always surrounded by green border. Upper surface green portion of emerging leaves are ca. green group RHS 144A; yellow portion is yellow group RHS 5A; lower surface green group 144A and yellow group RHS 5D.

Yellow and green colors darken with leaf maturity. First fully expanded leaves darken to green group RHS 137 in green portions. See lower leaves in FIG. 1. Similarly third fully expanded leaves (upper surface) green portions darken to darker than green group RHS 139A, and yellow portions RHS 13A. A red tinge first starts appearing on the lower surface of about third fully expanded leaves; color being darker on the midrib and fades out going into blade. Midrib is grayed orange group RHS 169A, with yellow portions yellow group RHS 16B. Green portions turn yellow green group RHS 144A with grayed orange specs of RHS 169A.

By $4^{th}$ and $5^{th}$ fully expanded leaves red tinge starts appearing on upper surface as well, midrib is red purple group RHS 59B and fades out into yellow portions. Upper yellow portions are yellow orange group RHS 17B with specs of red purple RHS 59B. Green portions darken so much and with color mixtures, almost turn black, lighter than black group RHS 202A. Lower green portions turn grayed purple RHS187A, midrib darkens to red purple group RHS 60A and fades out into yellow orange group RHS 17D.

All color codes refer to "The Royal Horticultural Society London 1986". Colors and leaf size may vary somewhat depending on horticultural practices such as light levels and fertilizer rates, among other things, without however, any variance in genotype. The age of the plant observed for the detailed botanical description was 18 weeks, and was grown under greenhouse conditions.

I claim:

1. A new and distinct cultivar of Codiaeum plant named 'Croton Zulu' as shown and described, particularly characterized by its bushy growth habit forming a rounded plant, and unique, uneven variegation beginning yellow and maturing to red and orange colors.

* * * * *